(12) United States Patent
Tang (10) Patent No.: US 10,395,773 B2
(45) Date of Patent: Aug. 27, 2019

(54) AUTOMATIC CHARACTERIZATION OF AGATSTON SCORE FROM CORONARY COMPUTED TOMOGRAPHY

(71) Applicant: INTERNATIONAL BUSINESS MACHINES CORPORATION, Armonk, NY (US)

(72) Inventor: Hui Tang, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 5 days.

(21) Appl. No.: 15/804,860

(22) Filed: Nov. 6, 2017

(65) Prior Publication Data

US 2019/0138694 A1    May 9, 2019

(51) Int. Cl.
*G06T 7/00* (2017.01)
*G16H 50/30* (2018.01)
(Continued)

(52) U.S. Cl.
CPC ............. *G16H 50/30* (2018.01); *A61B 6/032* (2013.01); *A61B 6/503* (2013.01); *A61B 6/504* (2013.01); *A61B 6/5217* (2013.01); *A61B 6/5235* (2013.01); *G06F 19/321* (2013.01); *G06K 9/6256* (2013.01); *G06K 9/6267* (2013.01); *G06T 7/0014* (2013.01); *G06T 7/136* (2017.01); *G06K 2209/051* (2013.01);
(Continued)

(58) Field of Classification Search
None
See application file for complete search history.

(56) References Cited

U.S. PATENT DOCUMENTS

2007/0225598 A1\* 9/2007 Buelow ..................... G06T 7/11
600/425
2008/0159610 A1\* 7/2008 Haas ................... A61B 5/02007
382/131

(Continued)

FOREIGN PATENT DOCUMENTS

CN    104933751 A    9/2015
CN    104091346 B    2/2017

OTHER PUBLICATIONS

Wolterink, Jelmer M. et al., "An evaluation of automatic coronary artery calcium scoring methods with cardiac CT using the orCaScore framework," Medical Physics 43.5 (May 2016): 2361-73.
(Continued)

*Primary Examiner* — Delomia L Gilliard
(74) *Attorney, Agent, or Firm* — Erik Huestis; Stephen Kenny; Foley Hoag LLP (57) ABSTRACT

Automatic characterization of the Agatston score from coronary computed tomography (CT) is provided. In various embodiments, a plurality of coronary computed tomography images are segmented into a plurality of segments corresponding to features of coronary anatomy. A plurality of calcium candidates are extracted from the plurality of coronary computed tomography images by thresholding. Coronary calcification is located in the coronary computed tomography images by applying a trained classifier to the plurality of calcium candidates. An Agatston score is computed from the located calcification.

20 Claims, 8 Drawing Sheets

(51) Int. Cl.
    *G06T 7/136*     (2017.01)
    *G06K 9/62*      (2006.01)
    *A61B 6/03*      (2006.01)
    *A61B 6/00*      (2006.01)
    *G06F 19/00*     (2018.01)

(52) U.S. Cl.
    CPC .............. *G06T 2207/10081* (2013.01); *G06T 2207/20128* (2013.01); *G06T 2207/20132* (2013.01); *G06T 2207/30048* (2013.01); *G06T 2207/30101* (2013.01)

(56) References Cited

U.S. PATENT DOCUMENTS

| | | | |
|---|---|---|---|
| 2013/0094749 A1* | 4/2013 | Oh .................... | A61B 6/503 382/133 |
| 2016/0045180 A1* | 2/2016 | Kelm .................. | G06T 7/11 600/408 |
| 2018/0182103 A1* | 6/2018 | Syeda-Mahmood ... | G06T 15/20 |

OTHER PUBLICATIONS

Giannoglou, Vasilis G. et al., "Genetic fuzzy rule based classification systems for coronary plaque characterization based on intravascular ultrasound images," Engineering Applications of Artificial Intelligence 38 (Feb. 2015): 203-20.

Aizhong Mi et al., "A multiple classifier fusion algorithm using weighted decision templates," Scientific Programming 2016 (2016): 3943859.

\* cited by examiner

AUTOMATIC CHARACTERIZATION OF AGATSTON SCORE FROM CORONARY COMPUTED TOMOGRAPHY

BACKGROUND

Embodiments of the present disclosure relate to detection of calcification of the coronary arteries, and more specifically, to automatic characterization of the Agatston score from coronary computed tomography (CT).

BRIEF SUMMARY

According to embodiments of the present disclosure, methods of and computer program products for automatic calcium detection are provided. In various embodiments, a plurality of coronary computed tomography images are segmented into a plurality of segments corresponding to features of coronary anatomy. A plurality of calcium candidates are extracted from the plurality of coronary computed tomography images by thresholding. Coronary calcification is located in the coronary computed tomography images by applying a trained classifier to the plurality of calcium candidates. An Agatson score is computed from the located calcification.

DETAILED DESCRIPTION

Detection of calcified plaques in coronary arteries is helpful in cardiovascular disease risk assessment. Calcification in the coronary arteries provides a biomarker for coronary artery disease. The amount of calcium in coronary artery is related to the risk of future cardiovascular disease. Computed tomography (CT) is an efficient and reproducible modality for calcified plaques for coronary arteries. Quantification measures of calcium, such as Agatston score, mass and volume are positively correlated with the mortality rate and thus are important for prognosis.

In general, the Agatston score is calculated using a weighted value assigned to the highest density of calcification in a given coronary artery. The density is generally measured in Hounsfield units (HU). A score of 1 is assigned for 130-199 HU; 2 for 200-299 HU; 3 for 300-399 HU; and 4 for 400 HU and greater. This weighted score is multiplied by the area (in square millimeters) of the coronary calcification. The calcium score of every calcification in each coronary artery for all of the tomographic slices is summed up to give the total coronary artery calcium (CAC) score. Variations of the Agatston score may also be employed, including those based on mass or volume, or those that are lesion-specific. It will be appreciated that alternative methods have various advantages in different clinical contexts.

Assessment of Agatston score may be performed by radiologists using computed tomography (CT) and computed tomography angiography (CTA) images. However, manual quantification of the calcium score is tedious and error-prone. Moreover, using both CT and CTA entails an increase in cost and radiation exposure.

Accordingly, the present disclosure provides an automatic solution for calcium assessment in CT images. In various embodiments, the whole chest is modeled, including all heart chambers and main arteries. Accordingly, instead of localizing calcium candidates with respect to the coronary artery alone, their position is assessed with respect to other anatomies, segmented from CT images using joint atlas label fusion methodology. This comprehensive spatial information together with other features such as shape, size and texture of each calcium candidate is used with a random forest classifier trained to detect coronary calcification.

As set out below, methods according to the present disclosure have a precision of 95.1% and a recall of 89.0% in classifying calcium candidates found based on thresholding within an exemplary dataset. In the example provided below, all test patients with true calcification were detected as positive, yielding a patient level sensitivity of 100%. Among the test patients without calcification, 44 out of 56 patients resulted in no calcium finding, yielding a patient level specificity of 78.6%. The whole heart Agatston score was quantified for the manual and automatically detected calcium on the 22 diseased test cases. A Pearson correlation coefficient of 0.98 was observed. Accordingly, the present disclosure enables reliable detect of calcification using CT data.

Detection of calcium spots in CT alone has the benefit of reducing the radiation dose and the cost as compared to CT+CTA. The primary limitation of CT is that compared to CTA, arteries are less contrasted in CT, thus each candidate's accurate location with respect to coronary artery is not available. However, advanced methods of anatomy segmentation, specifically joint atlas label fusion provides the ability to define anatomies other than the coronary artery within CT images, thus specifying the overall position of the calcium candidate in the heart and indirectly with respect to the coronary artery.

In the present disclosure, automatic segmentation with joint atlas label fusion is used to define new spatial features for the calcium candidates that accurately characterize their position with respect to four heart chambers and major arteries. Using these features, along with shape and intensity, CT alone can provide a performance comparable to CT+CTA in calcium detection. The computational methodology described herein can also be used when CTA is available.

Exemplary methods for calcium detection and Agatston score quantification comprise four steps. In the first step, eight anatomies in the chest are segmented, including the aorta, the coronary artery, the pulmonary artery, the four chambers of the heart, and the myocardium. In the second step, the calcium candidates are extract and their features are calculated. Third, a binary classification is performed on each candidate to detect the calcium in the coronary artery. Fourth, the whole heart Agatston score is quantified and a risk category is assigned.

As noted above, the coronary artery lumen is difficult to detect in CT scans without a contrast agent. Due to low contrast and the small size of coronary arteries, registration from the CTA atlas to non-contrast CT is challenging and imprecise. However, the registration for large organs such as the heart and aorta is less challenging and more precise. Thus, in various embodiments, CTA atlases are generated with the eight anatomies mentioned above. In some embodiments, the atlas count is 21. All the atlases are automatically cropped to a bounding box defined by the lungs so that images from different atlases share approximately the same field of view. The lung is automatically segmented using a simple threshold in CTA as they have fixed range of Hounsfield unit.

The CTA atlases are registered to the target CT image in two steps. In the first step, a rigid registration is performed using mutual information as the similarity metrics, with deformation used as an initialization for the following non-rigid registration. The non-rigid registration uses a BSpline transform with mutual information as the similarity metric. In various embodiments, the registrations are performed using Elastix.

After the registration, an approximate segmentation of the target image is obtained by a joint label fusion method. The segmentation from label fusion is then post-processed to obtain a smoother boundary.

Figure 1A:
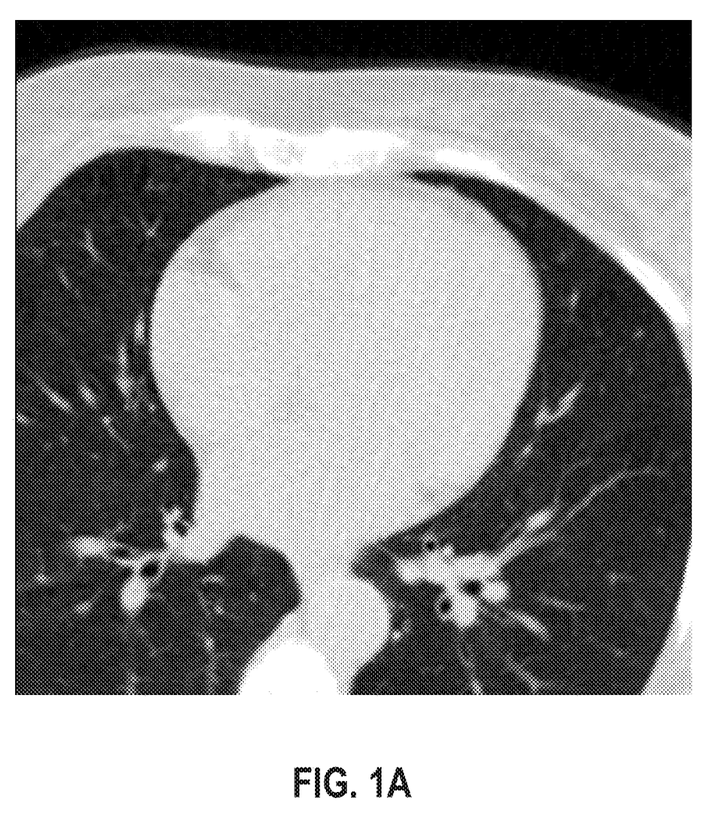
FIGS. 1A-C illustrate an exemplary segmentation according to embodiments of the present disclosure.
Figure 1B:
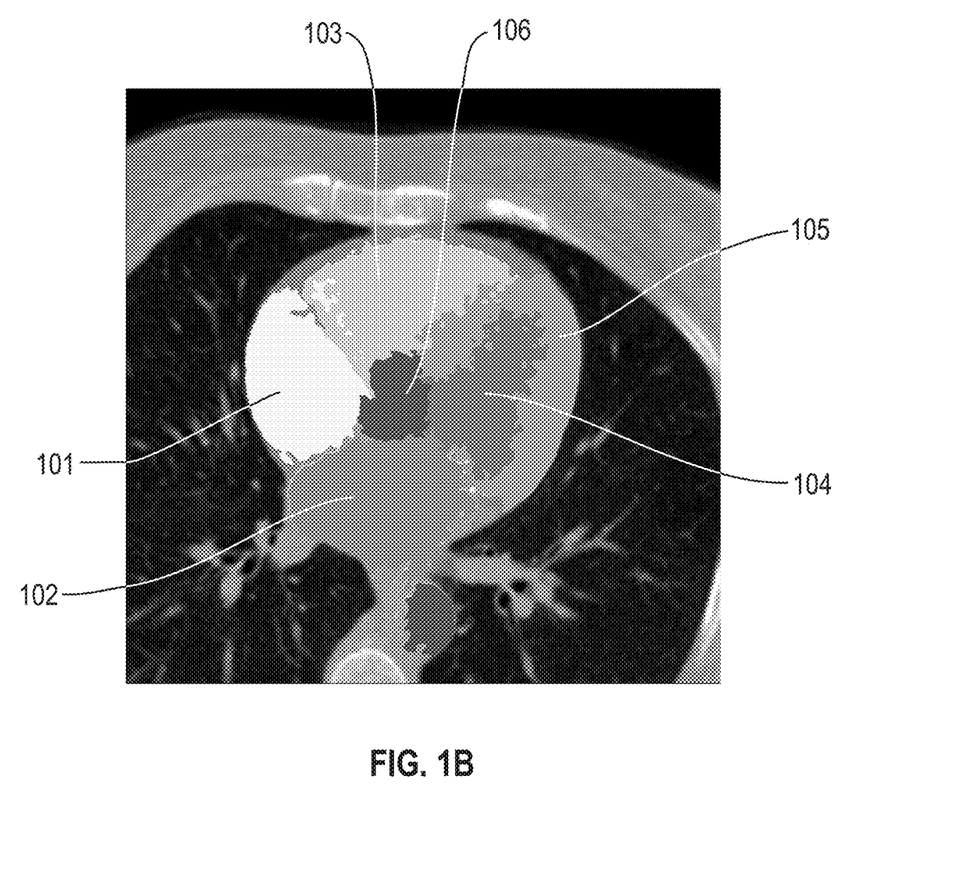
Figure 1C:
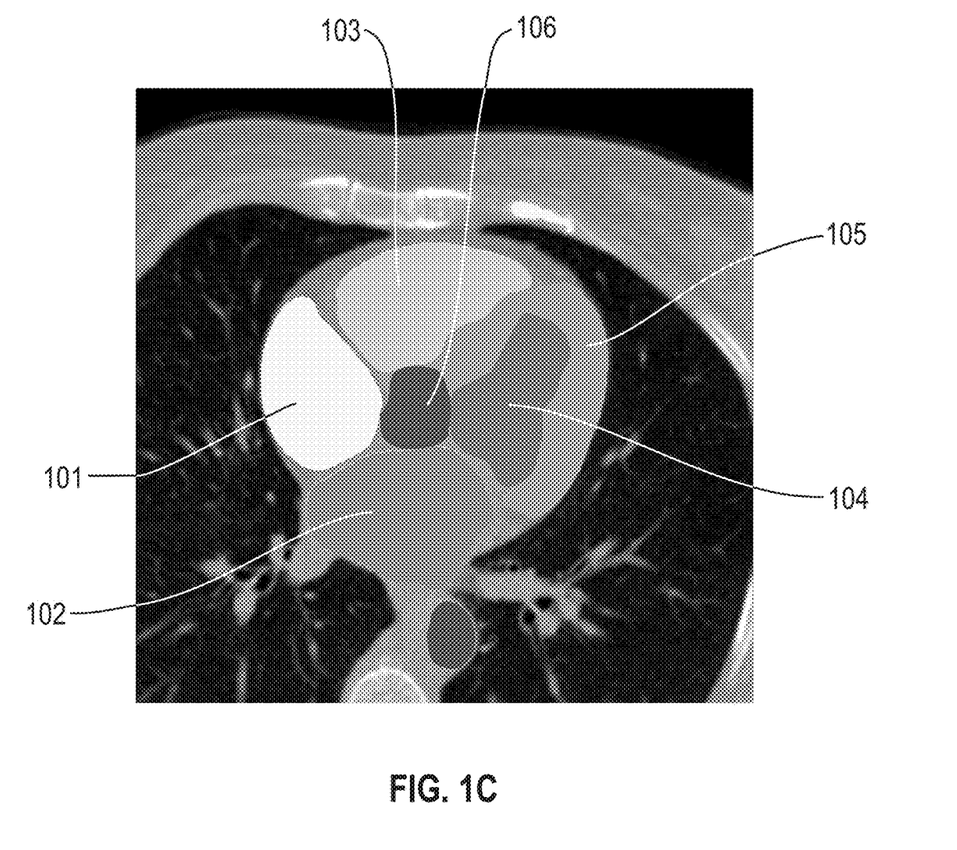

With reference now to FIG. 1 a segmentation according to embodiments of the present disclosure is illustrated. In FIG. 1A, a source CT image is shown. In FIG. 1B, segmentation results of multi-atlas label fusion is shown. In FIG. 1C, smoothed segmentation of the heart, pulmonary artery, aorta, and coronary artery are shown. In these exemplary figures, the coronary artery and pulmonary artery are not shown. The right atrium 101, left atrium 102, right ventrical 103, left ventrical 104, myocardium 105, and aorta 106 are visible.

Figure 2A:
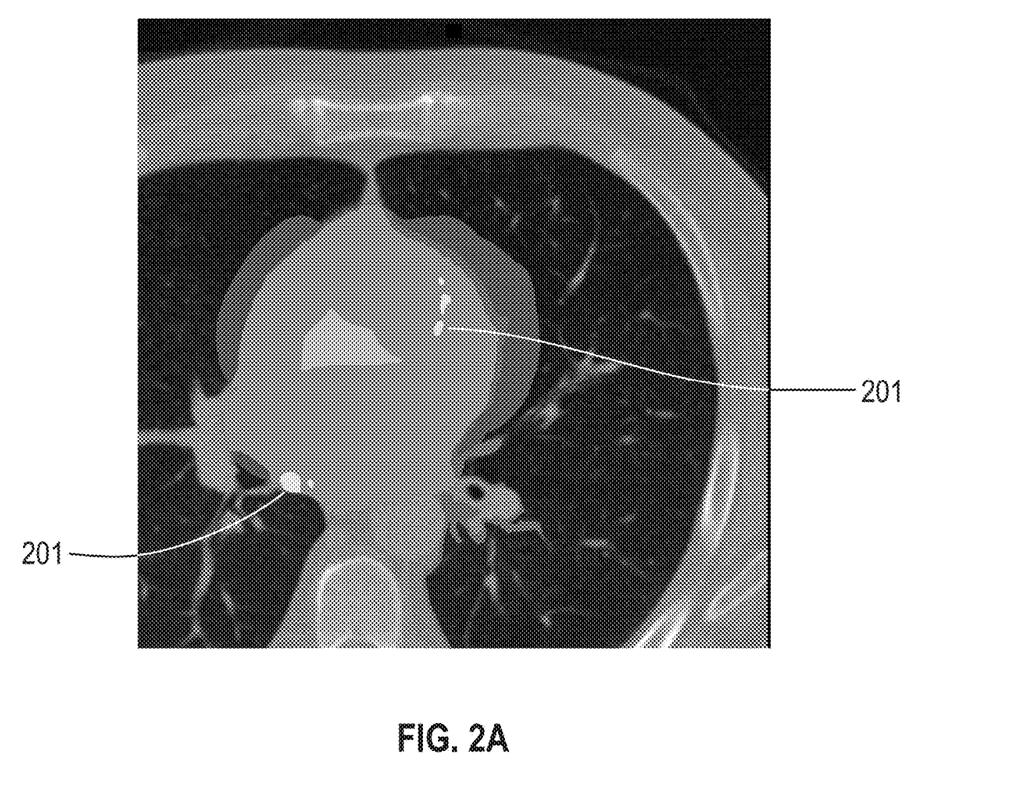
FIGS. 2A-B illustrate exemplary calcium candidates determined according to embodiments of the present disclosure.
Figure 2B:
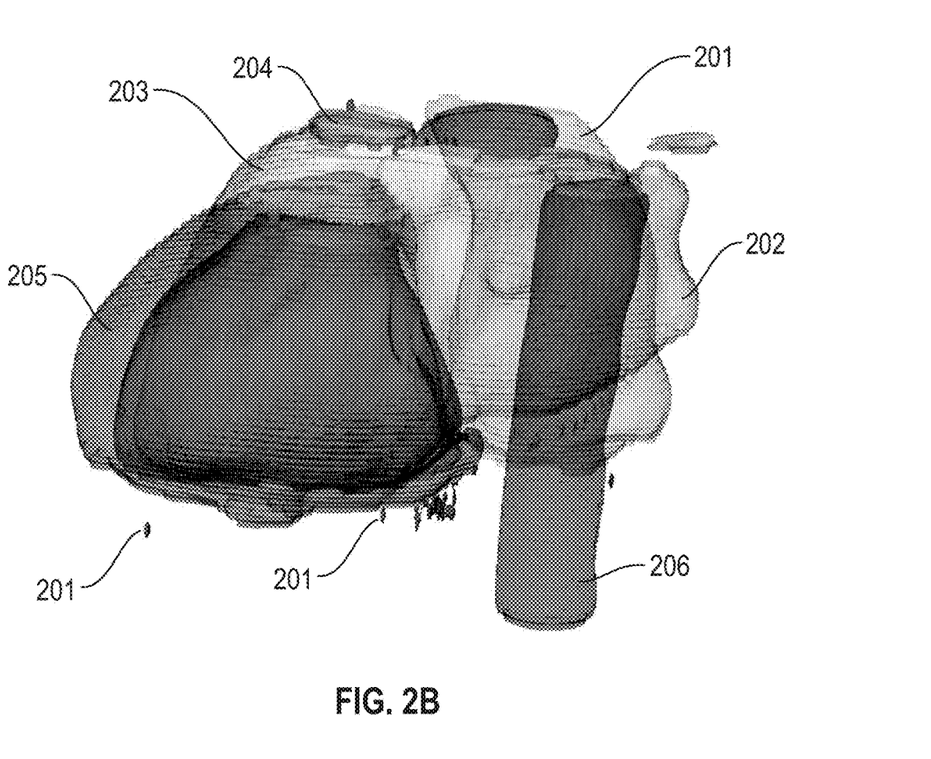

In FIG. 2, calcium candidates are illustrated. In FIG. 2A, calcium candidates 211 are depicted as generated from the segmentation. In FIG. 2B, the calcium candidates 211 are presented in a 3D surface model built from the segmentation. The right atrium 201, left atrium 202, right ventrical 203, left ventrical 204, myocardium 205, and aorta 206 are visible.

Calcium has a density over 130 HU. Thus, in some embodiments, an independent connected component analysis is performed to get all of the objects whose HU is above 130.

It will be appreciated that a variety of approaches to connected-component labeling are known. In general, any method that are uniquely labels subsets of connected components are suitable for use according to the present disclosure. For example, a thresholding step may be applied to the image, in this case the threshold corresponding to HU greater than 130. Blob extraction is then performed on the resulting binary image. Various approaches appear in the literature, including watershed analysis and two-pass algorithms.

A region of interest (ROI) is defined to include the heart. In some embodiments, the ROI extends about 20 mm beyond the heart's outer boundary. In some embodiments, objects are excluded that have a volume less than a predetermined threshold. For example, in some embodiments, objects having a volume less than about 1.5 mm$^3$, as objects in this range are likely caused by noise. Likewise, objects having a volume above a predetermined threshold may be excluded. For example, in some embodiments, objects having a volume greater than about 1,000 mm$^3$ are excluded, as objects in this range are likely to be stents or bone.

For each object so identified, the below described features are extracted. In some embodiments, these features are extracted for the original scale. In some embodiments, these features are extracted for one or more smoothed versions. For example, in some embodiments, these features are extracted for the original scale in addition to smoothed versions of the image at scales ranging from 1 mm to 3.5 mm with a step of 0.5 mm.

In some embodiments, a neighborhood is defined around each candidate. The same statistical features are extracted for the neighborhood surrounding each candidate in order to characterize the neighborhood. In some embodiments, a plurality of neighborhood scales are analyzed, for example, 20×20×20 mm$^3$ and 30×30×30 mm$^3$.

In some embodiments, the features include average, minimum and maximum intensity as well as the standard deviation of intensities for each calcium candidate.

In some embodiments, the features include volume of each calcium candidate. In some embodiments, volume of the region with intensity above T in each calcium candidate is also included. In an exemplary embodiments, T ranges from 130 HU to 190 HU with a step of 5 HU.

In some embodiments, shape features for each calcium candidate are included. Such shape features may include blobness and tublarness. In various embodiments, these features are based on the magnitude of the three eigenvalues ($\lambda 1$, $\lambda 2$ and $\lambda 3$) of the candidate shape, obtained through principal component analysis.

In some embodiments, the features include compactness, which shows measures how much a calcium candidate region is compact. In some embodiments, compactness is defined by the volume divided by $4\pi*\lambda 1*\lambda 2*\lambda 3$. This yields a number between 0 and 1, approaching one for a fully spherical object without holes or openings.

In some embodiments, the features include displacement from the heart center. The heart center is defined as the center of mass of the heart. This feature contains the Euclidean distance of each object centroid to the heart center and also the shift in x, y and z axis.

In some embodiments, the features include spatial features. In some embodiments, for every object, the average distance of each voxel is computed to the chest anatomies including the four heart chambers, myocardium, aorta, pulmonary artery and coronary artery. The segmentation with and without smoothing may both be used.

In some embodiments, the features include anatomy probability features. For example, in some embodiments, each voxel x gets an anatomy label i, 0<i<7 for each registered atlas. Given 21 atlases, a probability is calculated for a specific anatomy label for each voxel (px, 0<i<7) by dividing the number of votes for that label by 21, followed by a Gaussian smoothing. IN some embodiments, smoothing has a scale of 1 mm. The average per anatomy probability for the calcium candidate and the appropriate neighborhoods are used as features. As noted above, the neighborhoods may have a size of, for example, 20×20×20 mm$^3$ or 30×30×30 mm$^3$ around the candidate.

In embodiments including all features described above, there are 144 features. Due to the high dimension and various scales of the extracted features, a random forest classifier is used in various embodiments. The random forest has the advantage of handling various feature scales and feature selection automatically. In the exemplary embodiment described below, the classifier used consists of 400 decision trees.

Other parameters, including tree depth and the size of the feature bag, may be optimized using grid search in the training dataset.

Referring to Table 1, data divisions in exemplary training and testing sets are shown.

TABLE 1

| Performance | Modality | No Calcium | Mild | Moderate | Severe | Total |
|---|---|---|---|---|---|---|
| Training | CT | 20 | 24 | 13 | 47 | 104 |
|  | CTA | 10 | 13 | 8 | 26 | 57 |
| Testing | CT | 56 | 6 | 4 | 12 | 78 |
|  | CTA | 35 | 4 | 2 | 7 | 48 |
| Total | CT | 76 | 30 | 17 | 59 | 182 |
|  | CTA | 45 | 17 | 10 | 33 | 105 |

The example dataset consists of CT data from 182 patients, imaged at a collaborating clinical institution. The images had various scanning protocols on scanners from multiple vendors. The in-plane image resolution ranges from 0.28 mm to 0.47 mm, and the slice thickness ranges from 1 mm to 3 mm. Among the 182 patients, 105 of them have an additional CTA scan, this provides the possibility to compare methods in scenarios with and without CTA.

Among the 182 patients, 76 patients have no calcium (Agatston score=0), 30 patients have mild calcium (0<Agatston score≤100), 17 patients have moderate calcium (100<Agatston score≤300) and 59 patients have severe calcium (Agatston score>300) based on their Agatston Score reported by an experienced radiologist. The Agatston score is quantified using the method described in. The data is divided into the training and testing groups according to Table 1.

The ground truth calcium was annotated by an experienced radiologist with 5 years of general and musculoskeletal radiology experience in an in-house developed annotation tool. The candidate calcium objects were highlighted and shown to the radiologist. The radiologist can scroll down and up the image to visually identify the ground truth calcium and pick it by one single click inside the candidate region. The radiologist reviewed each image at least twice, with a four month period in between, to ensure the accuracy of annotations.

The performance of the methods described herein are evaluated in several ways. The first experiment evaluates the performance in the non-contrast CT and uses all the data. The second experiment compares performance in results with and without contrast agent for the same set of patients, and uses only cases with both CT and CTA. In this experiment, since the atlases are also built in CTA, improved segmentation is expected. All features are still extracted from CT alone.

For each of the two experiments, a separate classifier is trained on the corresponding training set. The optimal parameters are tuned in the training set using 5-fold-patient cross validation strategy.

In the testing dataset, three measures are computed: precision, recall, and F1 value. The overall precision, recall, and F1 are calculated as weighted average of each patient's results. The weight values are defined as the volume of calcium found in the patient and the number of calcium ground truth objects in each patient. The overall true positive, true negative, false positive and false negative rates are calculated. These are then used to calculate overall results for the precision, recall and F1 value.

On the patient level, all of the 22 cases in the exemplary data with calcium in the testing scan are detected to be with calcium and 44 out of 56 (78.6%) calcium-free cases are detected to be calcium free. Even if one of the candidates is misclassified, the case is counted as a false positive. Considering that each scan has multiple, typically 100+, calcium candidate samples for the classification, this is a very high patient level specificity.

Table 2 summarizes the performance of this method in the calcium candidate level. It shows an overall precision of 93.9%.

TABLE 2

| Performance | Precision | Recall | F1 |
|---|---|---|---|
| NumberWeighted | 95.1% | 89.0% | 91.2% |
| VolumeWeighted | 94.5% | 90.5% | 91.9% |
| Total | 93.9% | 89.0% | 91.4% |

Figure 3:
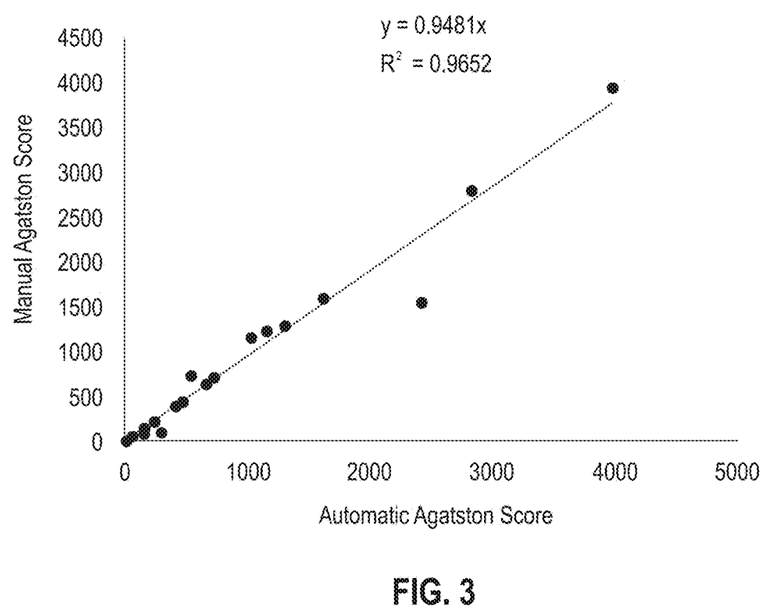
FIG. 3 illustrates the correlation between a manually determined Agatson score and an automatically determined Agatson score according to embodiments of the present disclosure.

The whole heart Agatston score is also quantified based on manually annotated calcium and the automatically detected calcium. The Pearson correlation coefficient between the manual and automatic Agatston score is 0.98, and the scatter plot is shown in FIG. 3. All cases are assigned to the correct risk category according to the Agatston score.

The outcome is compared between data with and without contrast and the results are summarized below in Table 3. As the table shows, there does not seem to be any advantage in including CTA data in the segmentation stage. In fact, the performance shows a slight decline when CTA data is included, with total precision dropping from 95.6% to 93.3%. This result is probably driven by the fact that the features and classification framework are designed and optimized for CT data.

TABLE 3

| Performance | Modality | Precision | Recall | F1 |
|---|---|---|---|---|
| NumberWeighted | CT | 96.3% | 95.6% | 95.7% |
|  | CTA | 94.5% | 95.6% | 94.6% |
| VolumeWeighted | CT | 95.3% | 95.3% | 95.1% |
|  | CTA | 94.1% | 95.3% | 94.3% |
| Total | CT | 95.6% | 95.6% | 95.6% |
|  | CTA | 93.3% | 95.6% | 94.4% |

Figure 4:
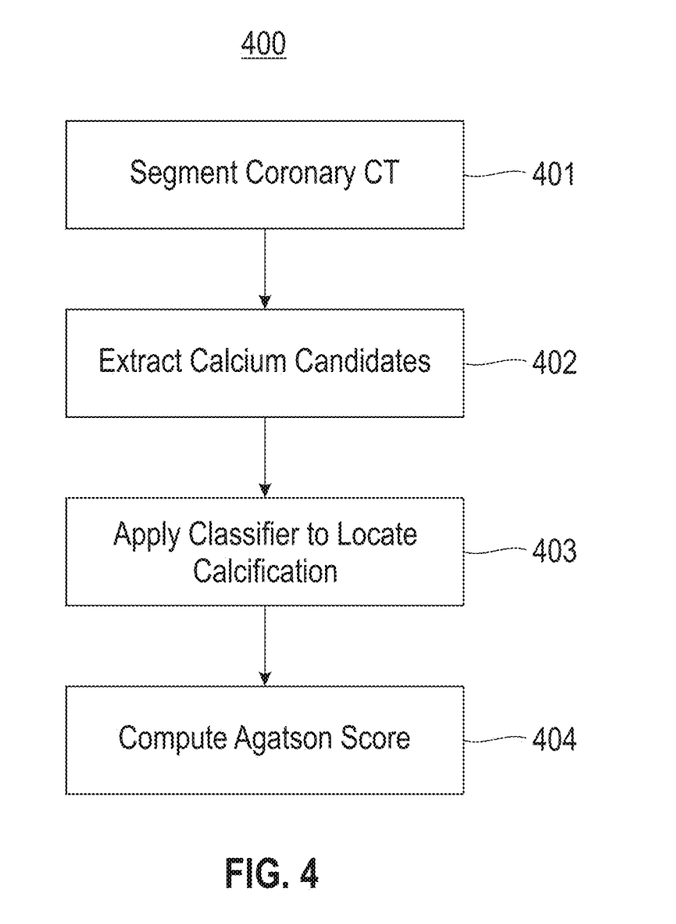
FIG. 4 illustrates a method of automatic calcium detection according to embodiments of the present disclosure.

Referring now to FIG. 4, a method of automatic calcium detection is illustrated according to embodiments of the present disclosure. At 401, a plurality of coronary computed tomography images are segmented into a plurality of segments corresponding to features of coronary anatomy. At 402, a plurality of calcium candidates are extracted from the plurality of coronary computed tomography images by thresholding. At 403, coronary calcification is located in the coronary computed tomography images by applying a trained classifier to the plurality of calcium candidates. At 404, an Agatson score is computed from the located calcification.

As set forth above, in various embodiments of the present disclosure, methods are provided for automatic calcium detection from CT scan. To overcome the calcium location ambiguity caused by invisibility of coronary artery in the CT scan, the heart anatomies are segmented and use the distance of each calcium candidate to these anatomies to better localize the calcium candidates. As shown in the example data, CT alone (without inclusion of CTA data at the time of segmentation) suffices for automatic calcium assessment.

The whole heart Agatston score is then computed. As set forth above, the Pearson correlation coefficient between the Agatston score obtained from manually identified calcium and automatically detected calcium is close to 1. Accordingly, methods according to the present disclosure are able to detect calcium from one single non-contrast CT scan with accuracy comparable to using both contrast and non-contrast CT scans.

Figure 5:
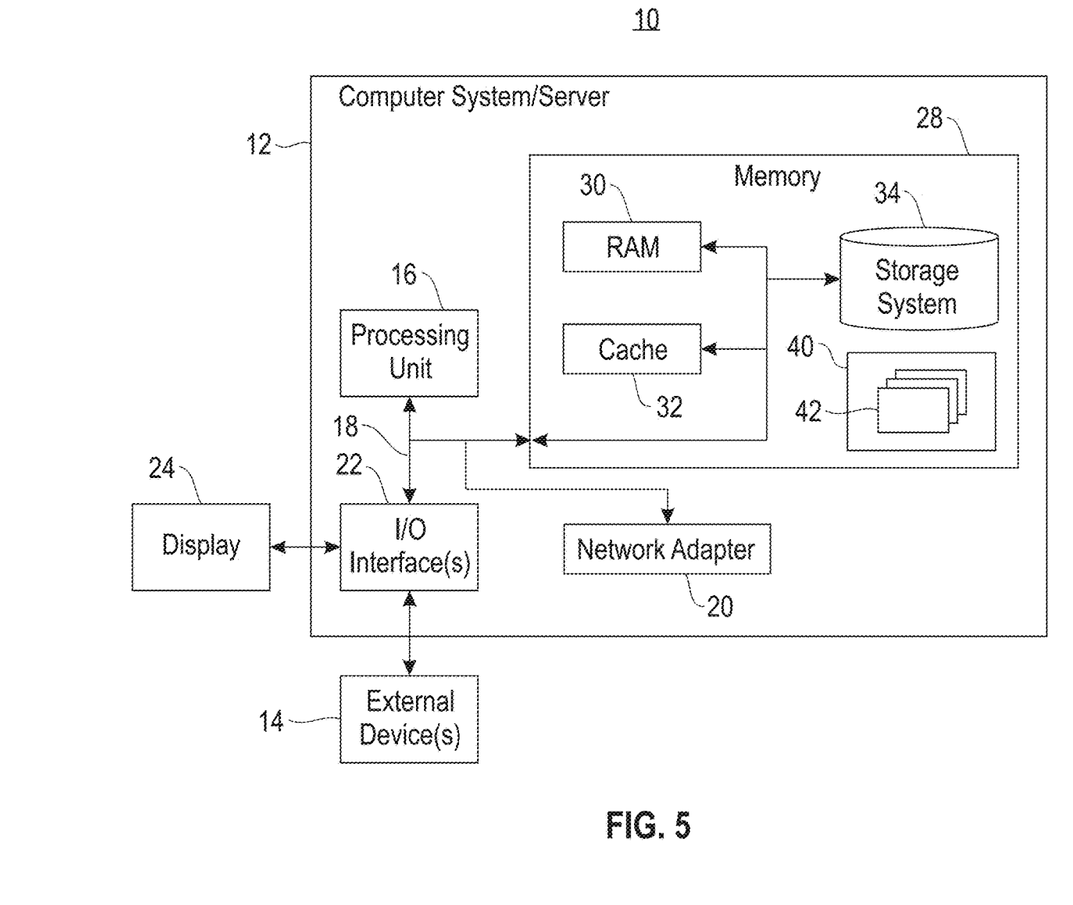
FIG. 5 depicts a computing node according to embodiments of the present disclosure.

Referring now to FIG. 5, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
    segmenting a plurality of coronary computed tomography images into a plurality of segments corresponding to features of coronary anatomy, wherein segmenting the plurality of coronary computed tomography images comprises applying an atlas;
    based on the plurality of segments, extracting a plurality of calcium candidates from the plurality of coronary computed tomography images by thresholding;
    locating coronary calcification in the coronary computed tomography images by applying a trained classifier to the plurality of calcium candidates;
    computing an Agatson score from the located calcification.

2. The method of claim 1, wherein the features of coronary anatomy comprise the aorta, the coronary artery, the pulmonary artery, the four chambers of the heart, or the myocardium.

3. The method of claim 1, wherein applying the atlas comprises performing joint atlas label fusion.

4. The method of claim 1, wherein the trained classifier is a random forest classifier.

5. The method of claim 1, wherein applying the trained classifier comprises computing a plurality of features of the plurality of calcium candidates and supplying the plurality of features to the trained classifier.

6. The method of claim 5, wherein the plurality of features comprises position relative to the features of coronary anatomy, shape, size, or texture.

7. The method of claim 1, wherein the plurality of coronary computed tomography images are without contrast.

8. The method of claim 1, wherein segmenting the plurality of coronary computed tomography images comprises cropping the plurality of coronary computed tomography images based on the location of a lung.

9. The method of claim 1, wherein segmenting the plurality of coronary computed tomography images comprises rigid registration.

10. The method of claim 1, wherein segmenting the plurality of coronary computed tomography images comprises non-rigid registration.

11. The method of claim 1, wherein segmenting the plurality of coronary computed tomography images comprises smoothing a preliminary segmentation.

12. The method of claim 1, wherein extracting the plurality of calcium candidates comprises independent connected component analysis.

13. The method of claim 1, wherein extracting the plurality of calcium candidates comprises excluding candidates having a volume below a predetermined threshold.

14. The method of claim 1, wherein extracting the plurality of calcium candidates comprises excluding candidates having a volume above a predetermined threshold.

15. The method of claim 1, wherein applying the trained classifier comprises computing a plurality of features of a neighborhood of calcium candidates and supplying the plurality of features to the trained classifier.

16. The method of claim 15, wherein the neighborhood of calcium candidates comprises a predetermined volume around each candidate.

17. The method of claim 5, wherein the plurality of features comprises average, minimum or maximum intensity, standard deviation of intensities, volume, blobness, tublarness, compactness, displacement from a heart center, spatial location position, or anatomy probability.

18. A system comprising:
 a computing node comprising a computer readable storage medium having program instructions embodied therewith, the program instructions executable by a processor of the computing node to cause the processor to perform a method comprising:
  segmenting a plurality of coronary computed tomography images into a plurality of segments corresponding to features of coronary anatomy, wherein segmenting the plurality of coronary computed tomography images comprises applying an atlas;
  based on the plurality of segments, extracting a plurality of calcium candidates from the plurality of coronary computed tomography images by thresholding;
  locating coronary calcification in the coronary computed tomography images by applying a trained classifier to the plurality of calcium candidates;
  computing an Agatson score from the located calcification.

19. A computer program product for automatic calcium detection, the computer program product comprising a computer readable storage medium having program instructions embodied therewith, the program instructions executable by a processor to cause the processor to perform a method comprising:
 segmenting a plurality of coronary computed tomography images into a plurality of segments corresponding to features of coronary anatomy, wherein segmenting the plurality of coronary computed tomography images comprises applying an atlas;
 based on the plurality of segments, extracting a plurality of calcium candidates from the plurality of coronary computed tomography images by thresholding;
 locating coronary calcification in the coronary computed tomography images by applying a trained classifier to the plurality of calcium candidates;
 computing an Agatson score from the located calcification.

20. The system of claim 18, wherein applying the atlas comprises performing joint atlas label fusion.

* * * * *